United States Patent [19]

Finney et al.

[11] 4,353,360

[45] Oct. 12, 1982

[54] PENILE ERECTILE SYSTEM

[75] Inventors: Roy P. Finney, Tampa, Fla.; Henry W. Lynch, Racine, Wis.

[73] Assignee: Medical Engineering Corporation, Milwaukee, Wis.

[21] Appl. No.: 202,591

[22] Filed: Oct. 31, 1980

[51] Int. Cl.[3] .................... A61F 5/00

[52] U.S. Cl. .................... 128/79; 3/1

[58] Field of Search .................... 128/79, 344, DIG. 25; 3/1

[56] References Cited

U.S. PATENT DOCUMENTS

| | | | |
|---|---|---|---|
| 3,853,122 | 10/1974 | Strauch et al. | 128/79 |
| 3,954,102 | 5/1976 | Buuck | 128/79 |
| 4,009,711 | 3/1977 | Uson | 128/79 |
| 4,066,073 | 1/1978 | Finney et al. | 128/79 |
| 4,201,202 | 5/1980 | Finney et al. | 128/79 |
| 4,267,829 | 5/1981 | Burton et al. | 128/79 |

*Primary Examiner*—Dalton L. Truluck
*Attorney, Agent, or Firm*—Quarles & Brady

[57] ABSTRACT

A penile erectile system which is adapted to be surgically implanted in man for the treatment of erectile impotence includes a penile implant comprising an elongated, flexible cylindrical member adapted to be implanted in the corpus cavernosum of a penis, said member including a pair of inner and outer chambers substantially filled with fluid and connected by a passage. The innermost of said chambers being non-distensible so that it is filled and pressurized by transferring fluid thereto from the outer chamber and it becomes rigid and supports the penis in an erectile state.

10 Claims, 6 Drawing Figures

PENILE ERECTILE SYSTEM

The present invention relates to a novel penile erectile system. More particularly, it relates to a unitized pressurizable implantable penile erectile system which is useful in the treatment of erectile impotence.

BACKGROUND OF THE INVENTION

Some cases of erectile impotence do not respond to conventional therapy and the surgical implanting of a penile erectile system may be the only practical means of remedying the impotency.

Several different types of penile erectile systems have been employed in the past. One type of penile erectile system which is currently available is an inflatable system. The inflatable system includes two fairly long inflatable and distensible tubes that are surgically implanted in the corpus cavernosum of the penis. Each of the two tubes is connected by tubing to a relatively large pressure bulb of inflating fluid which is implanted elsewhere in the body necessitating additional abdominal or scrotal surgery. The systems of U.S. Pat. No. 3,954,102 and U.S. Pat. No. 4,009,711 are representative of inflatable penile erectile systems.

Another type of penile erectile system in use comprises a pair of rods of suitable stiffness which are surgically implanted into the corpus cavernosum of the penis. A significant advantage of this system is that the amount of surgery involved is minimal as there is no pressure bulb to implant. A disadvantage of this system is that the permanent stiffness of the rods can be a source of physical pain and embarrassment to the patient. Representative penile erectile systems employing rod implants are the systems disclosed in U.S. Pat. No. 3,893,476 and U.S. Pat. No. 4,066,037.

SUMMARY OF THE INVENTION

It is the general object of the present invention to disclose a novel unitized pressurizable implantable penile erectile system.

It is a further object to disclose a unitized pressurizable implantable penile erectile system that can be implanted completely in the penis making abdominal or scrotal surgery unnecessary.

In its simplest form the entire penile erectile system of the present invention is contained in a single penile implant. However, two implants generally are used to provide a penile prosthesis.

The preferred implant of the penile erectile system of the present invention has a relatively short, proximal stem, a distal tip and an elongated flexible intermediate portion containing a pair of concentric cylindrical chambers. Both of the cylinders are substantially filled with hydraulic fluid and they are connected by a passage so that hydraulic fluid present in the outer chamber can be transferred to the inner chamber which is non-distensible to pressurize it and make it rigid.

The preferred implant also contains valve means for controlling the flow of fluid between the chambers so that the inner chamber can be pressurized and depressurized. Since the entire system is contained in the implant, it can be implanted as easily as the prior art penile rod implants. The only surgery required is that to place and position the implants in the corpus cavernosum of the penis.

When the implants are in place and the inner chamber is not pressurized the penis assumes a normal flaccid state. However, when the hydraulic fluid is transferred under pressure from the outer cylinder into the non-distensible inner cylinder, the inner cylinder becomes rigid causing the penis to assume an erectile position.

The penile erectile system of the present invention, in addition to being compact and thus minimizing the amount of surgery required, has a minimum number of fluid connections, thus reducing risk of leakage.

The foregoing and other objects and advantages will become apparent from the description which follows.

DESCRIPTION OF THE PREFERRED EMBODIMENTS

As seen in FIGS. 1–4, the preferred embodiment of the penile erectile system 10 comprises a pair of elongated implants 11, 11′. The two implants 11, 11′ are identical, therefore, only one will be described in detail.

Figure 1:
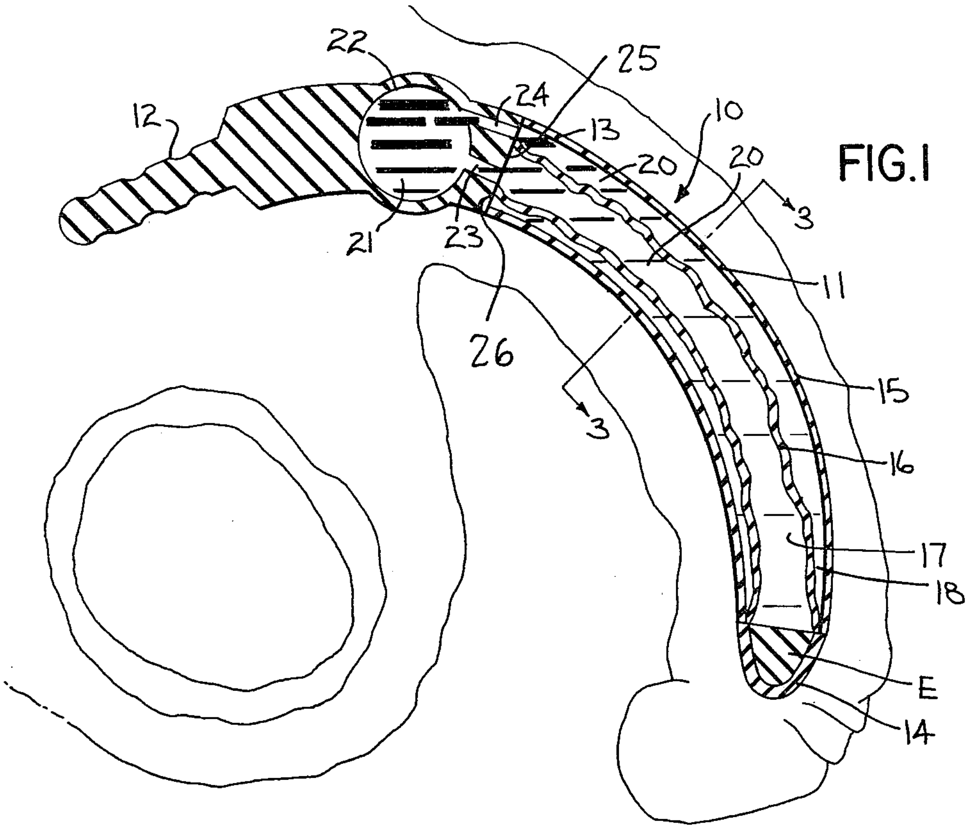
FIG. 1 is a side view, partly in section, of one embodiment of the penile erectile system of the present invention in a non-pressurized condition surgically implanted in a male.
Figure 2:
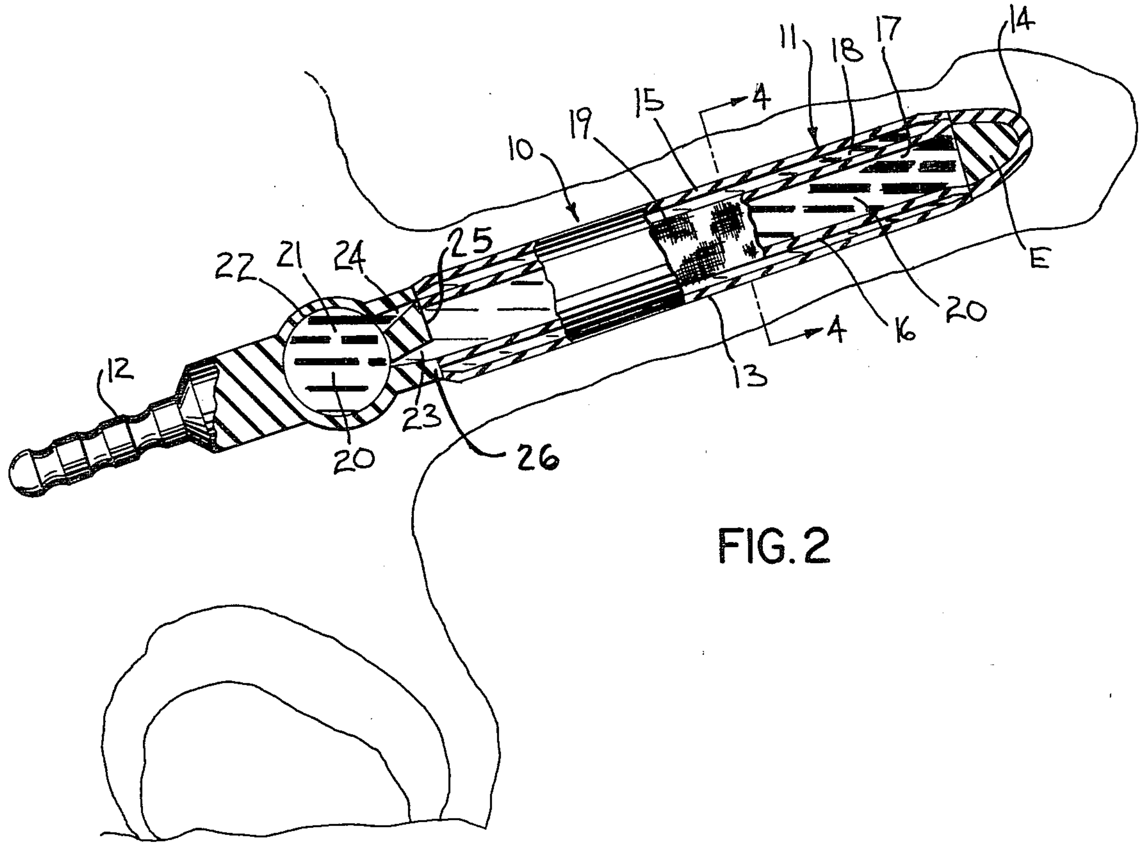
FIG. 2 is a side view similar to FIG. 1, except that the system is pressurized.
Figures 3, 4, 5, 6:
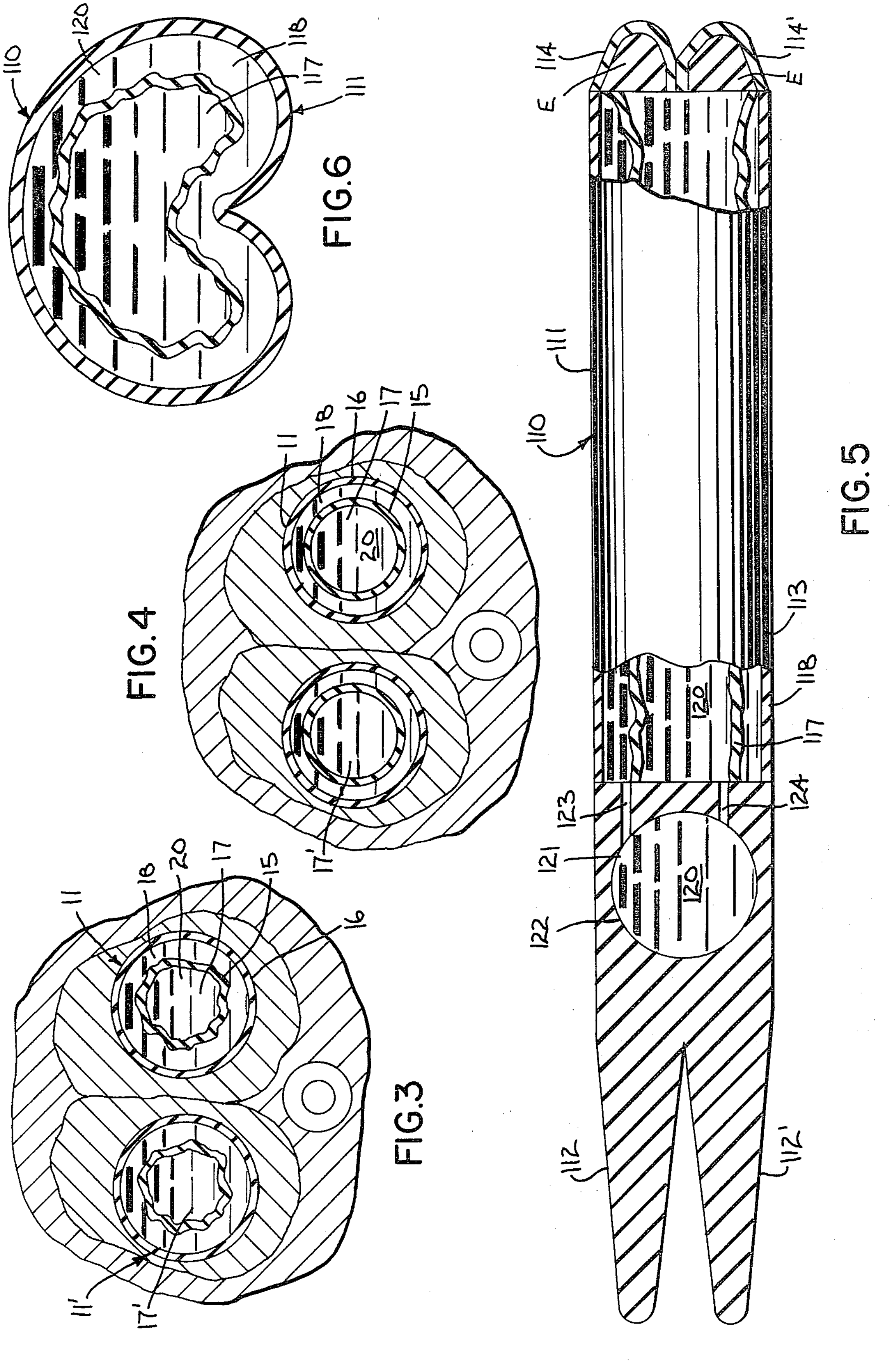
FIG. 3 is a cross sectional view taken along the line 3—3 in FIG. 1.
FIG. 4 is a cross sectional view taken along the line 4—4 in FIG. 2.
FIG. 5 is a top plan view, partly in section, of another embodiment of the system of the present invention.
FIG. 6 is a cross sectional view taken along line 6—6 in FIG. 5.

As seen in FIG. 1, the implant 11 has a short, proximal stem 12 of relatively stiff material which is implanted in the root end of a corpus cavernosum to support and anchor the implant, an intermediate cylindrical portion 13, and a conical distal tip 14. The tubular portion 13 and the tip 14 which are soft and flexible are implanted in the portion of the corpus cavernosum in the pendulus penis. As seen in FIGS. 2 and 4, each of the implants 11, 11′ is positioned in a separate corpus cavernosum of the penis.

The intermediate cylindrical portion 13 of the implant 11 includes a pair of concentric cylindrical sleeves 15 and 16 which are attached in a fluid tight manner to the stem 12 and to the tip 14 to form a pair of concentric chambers 17 and 18, respectively. The sleeve 15 which forms the wall of the inner chamber 17 is of a silicone coated mesh or woven fabric 19 which is inelastic and as a result the chamber 17 is non-distensible. The sleeve 15 also serves as the inner wall of the annular outer chamber 18. The sleeve 16 which is spaced outwardly from the sleeve 15 may be of a distensible material such as nonreinforced silicone rubber and it forms the outer wall of the annular chamber 18. The fluid tight seals between the sleeves 15 and 16 and the stem 12 and tip 14 may be made with a suitable silicone adhesive or by other conventional means.

As seen in FIGS. 1 and 3, even in a non-pressurized state the chambers 17 and 18 are substantially filled with a non-compressible biocompatible fluid 20 which may be saline or a free flowing silicone gel. When the non-distensible chamber 17 is not pressurized, the soft, flexible, intermediate tubular portion 13 of the implant 11 permits the penis to assume a substantially normal, flaccid position as seen in FIG. 1. However, when the chamber 17 is completely filled and pressurized, the penis assumes an erectile position as seen in FIG. 2.

As seen most clearly in FIG. 1, a passage 21 connects the chambers 17 and 18. The passage 21 is shaped to form a pump valve consisting of an enlarged intermediate bulbar portion 22 and a pair of throats 23 and 24 which communicate with the chambers 17 and 18 respectively.

As seen only in FIG. 1, when the system 10 is in its normal nonpressurized state the entire passage 21 including the bulbar portion 22 of the pump valve is filled with hydraulic fluid 20 and both of the throats 23 and 24 are open. In addition, in the nonpressurized state both the chambers 17 and 18 are substantially filled with the fluid 20. The system 10 is pressurized by repeatedly squeezing the bulbar portion 22 to pump hydraulic fluid 20 out of the outer chamber 18 through throat 23, bulbar portion 22 and throat 24 to fill non-distensible inner chamber 17 with fluid 20 under pressure. When the chamber 17 is sufficiently pressurized and rigid the bulbar portion 22 is released whereby the throat 23 is closed by pressure exerted by the hydraulic fluid 20 upon a resilient inner portion 25 of the end wall 26 of the chamber 17 adjacent the throat 23. As a result, the chamber 17 remains completely filled, pressurized and rigid, as seen in FIG. 2, until the wall portion 25 is manually deformed by squeezing to open the throat 23 and allow fluid 20 to flow back into the chamber 18 and the system 10 to resume a non-pressurized state.

The pressurizing of the nondistensible chamber 17 is facilitated by manually squeezing the outer chamber 18 to milk the fluid which is in that chamber through the throat 23, bulbar portion 22 and throat 24 into the chamber 18.

A variety of pump valves other than that shown in the drawing can be used including that disclosed in U.S. Pat. No. 4,167,952, which is incorporated by reference herein. Preferably, the pump valve is of the type which opens when it is squeezed, automatically closes when the squeezing stops and can be manipulated from the outside.

A second embodiment of the system of the present invention is seen in FIGS. 5 and 6. The system 110 seen therein is contained in a single implant 111 which has a pair of stems 112, 112' at the distal end, a pair of tips 114, 114' at the proximal end, and a common trunk or intermediate portion 113 which contains concentric chambers 117 and 118. The chambers 117 and 118 are connected by a passage 121 having a bulbar or pump portion 122 and throats 123 and 124. The valve means described in connection with the previous embodiment controls flow through the passage 121.

The system of the second embodiment is implanted in corpora cavernosam of the penis after removing the tissue separating the individual corpus.

The term "substantially filled" as used herein to describe the fluid content of a chamber means that a chamber contains about 60% to about 95% or more of its capacity of a non-compressible fluid such as water, saline or a free flowing gel. The actual content of fluid can vary; however, the distal portion of the implant when "substantially filled" should be still sufficiently flexible so that the penis can assume a normal flaccid position.

All the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The non-distensible inner chamber (17, 17' or 117) must provide when pressurized rigidity sufficient to maintain the penis in an erectile position. Therefore it must be of sufficient volume and size to perform this function either alone or in combination with another implant. In contrast, the outer chamber 18 serves primarily as a reservoir of pressurizing fluid for inner chamber and is sized accordingly. The exact dimensions of the chambers are not critical as long as they are adequate to provide the desired function of the chamber.

The sleeve 15 which forms the wall of the "non-distensible" chamber 17 is preferably made of a dacron mesh or fabric covered with silicone material so that it will not stretch when filled with fluid and pressurized. The sleeve 16 may be non-distensible or may be made of unreinforced silicone rubber. The diameters of the sleeves 15 and 16 can vary but are normally sized so that the implants when substantially filled will fill the corpus cavernosum in the non-pressurized state.

The proximal stems of the implants preferably have a Shore A hardness of about 70, the distal tips a Shore A hardness of about 20, and each of the materials has sufficient tensile strength for its intended use. In the preferred embodiments of the drawings, the tips are tapered and filled with a self-sealing silicone elastomer E to allow fluid to be added to or removed from the chambers with a fine needle and syringe.

The preferred method of implantation of the erectile system is through an incision made in the penis. After appropriate incision, the corpus cavernosum is dilated distally and proximally to accept the implant. The appropriate anatomical measurements are made to insure that the proximal stem of the implant or implants will be positioned at the base of the penis below the pelvic bone. An implant or implants having an appropriately sized intermediate section and distal tip is inserted into the corpus cavernosum of the penis. The distal tip is positioned in the tunica end of the corpus cavernosum. The proximal stem of the implant then is anchored in the root end of the corpus cavernosum.

The identical procedure is performed on the other side of the penis to complete the surgical procedure. The proximal stems of the two implants preferably will diverge laterally to accommodate the anatomy and provide lateral stability to the penis. When the embodiment utilizing a single implant is employed, the tissue separating the corpora cavernosam is removed before positioning the implant. The incision is then closed.

It is to be understood that the foregoing description has been for purposes of illustration and that a number of modifications and changes may be made without departing from the spirit and scope of the present invention. For example, although the implants described have solid stems for anchoring the implants, the stems could be hollow, if desired. In addition, although implants have been described and illustrated in which the outer chamber which serves as the reservoir is concentric relative to the inner chamber it will be appreciated that the reservoir role could be provided by one or more radially disposed smaller individual outer chambers if desired.

The invention is not to be limited by any of the specific embodiments described but only by the claims which follow.

I claim:

1. A penile erectile system comprising a penile implant including an inner chamber and a radially disposed outer chamber, the inner chamber being non-distensible so that when pressurized and filled with fluid it becomes rigid and the outer chamber having sufficient volume to accommodate enough fluid to fill and pressurize the inner chamber; a passage providing communication between said inner and outer chambers and means for retaining the transferred fluid from the outer chamber in the inner chamber to pressurize it and make it rigid.

2. The implant of claim 1 which includes means for controlling fluid through said passage.

3. The implant of claim 1 in which both chambers are normally substantially filled with hydraulic fluid and the outer chamber contains sufficient fluid which can be transferred to completely fill and pressurize the inner non-distensible chamber.

4. The implant of claim 1 in which the means for retaining the fluid is a pump valve positioned in the passage.

5. The implant of claim 1 which includes an anchoring stem.

6. The implant of claim 1 which includes a tapered tip.

7. A penile erectile system comprising a penile implant having an elongated cylindrical body with an anchoring stem at the proximal end; a tapered tip at the distal end; a pair of concentric chambers located intermediate the length of said body between the stem and the tip, the innermost of said chambers being non-distensible so that when pressurized and filled with fluid it becomes rigid and the outermost chamber having a volume sufficient to accommodate enough transferable fluid to completely fill and pressurize the innermost chamber; a passage providing communication between the innermost and outermost chambers and means for retaining fluid transferred from the outermost chamber into the innermost chamber to keep it pressurized and rigid.

8. The implant of claim 7 in which the means for retaining fluid in the innermost chamber is a pump valve.

9. The implant of claim 7 in which both chambers are normally substantially filled with hydraulic fluid.

10. The implant of claim 7 in which the implant has a pair of stems, a pair of tips and a common intermediate truck which includes the concentric chambers.

* * * * *